United States Patent
Heaton

(10) Patent No.: US 7,637,931 B2
(45) Date of Patent: Dec. 29, 2009

(54) PORTABLE THERAPEUTIC COOLING SYSTEM

(75) Inventor: Keith Patrick Heaton, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 723 days.

(21) Appl. No.: 11/175,084

(22) Filed: Jul. 5, 2005

(65) Prior Publication Data

US 2006/0004426 A1   Jan. 5, 2006

Related U.S. Application Data

(60) Provisional application No. 60/585,166, filed on Jul. 2, 2004.

(51) Int. Cl.
*A61F 7/00* (2006.01)
(52) U.S. Cl. ............... 607/104; 607/96; 607/109
(58) Field of Classification Search ........... 607/107, 607/104, 109
See application file for complete search history.

(56) References Cited

U.S. PATENT DOCUMENTS

| | | | | |
|---|---|---|---|---|
| 222,690 | A | * | 12/1879 | Goldschmidt ............ 607/104 |
| 3,468,299 | A | * | 9/1969 | Amato .................... 126/204 |
| 4,905,475 | A | * | 3/1990 | Tuomi ..................... 62/3.3 |
| 5,350,417 | A | * | 9/1994 | Augustine ............... 607/104 |
| 5,383,918 | A | * | 1/1995 | Panetta .................. 607/104 |
| 5,626,021 | A | * | 5/1997 | Karunasiri et al. ......... 62/3.5 |
| 5,913,885 | A | | 6/1999 | Klatz et al. |
| 6,581,400 | B2 | * | 6/2003 | Augustine et al. ......... 62/259.3 |
| 6,581,677 | B2 | * | 6/2003 | Dukes-Dobos et al. ..... 165/11.1 |
| 6,682,552 | B2 | | 1/2004 | Ramsden et al. |
| 6,730,115 | B1 | * | 5/2004 | Heaton .................. 607/104 |
| 7,179,279 | B2 | * | 2/2007 | Radons et al. ............ 607/108 |
| 2003/0135252 | A1 | * | 7/2003 | MacHold et al. .......... 607/106 |
| 2004/0025516 | A1 | * | 2/2004 | Van Winkle .............. 62/3.3 |
| 2004/0064170 | A1 | | 4/2004 | Radons et al. |

FOREIGN PATENT DOCUMENTS

| | | | |
|---|---|---|---|
| GB | 2313549 A | * | 12/1997 |
| JP | 09-072152 | | 10/1998 |
| JP | 10-250455 | | 2/2000 |
| WO | WO 94/05238 A1 | | 3/1994 |
| WO | WO 98/56310 A1 | | 12/1998 |
| WO | WO 99/09916 A1 | | 3/1999 |
| WO | WO 99/44552 A1 | | 9/1999 |
| WO | WO 01/50988 A1 | | 7/2001 |

OTHER PUBLICATIONS

For purpose of the column and line numbers the US publication equivalent 6,730,115 of GB2313549A has been used.*

Dietrich, et al: Effects of Normothermic Versus Hyperthermic Forebrain Ischemia in Rats, Stroke, vol. 21, No. 9, 1990; pp. 1318-1325.

(Continued)

*Primary Examiner*—Roy D Gibson
*Assistant Examiner*—Kaitlyn E Helling

(57) ABSTRACT

A disposable portable therapeutic cooling system that utilizes convective cooling and re-circulated air to efficiently, safely, and effectively cool the head and body of the patient, clothed or not, after a life-threatening health event, such as a cardiac arrest or stroke.

7 Claims, 4 Drawing Sheets

OTHER PUBLICATIONS

Reith, et al: "Body Temperature in Acute Stroke: Relation to Stroke Severity, Infarct Size, Morality, and Outcome"; The Lancet, vol. 347, Feb. 17, 1996; pp. 422-425.

Kammersgaard, et al: "Feasibility and Safety of Inducing Modest Hypothermia in Awake Patients with Acute Stroke Through Surface Cooling: A Case-Control Study"; Stroke, Sept. 2000; pp. 2251-2256.

Schwab, et al: "Brain Temperature Monitoring and Modulation in Patients with Severe MCA Infarction"; Neurology, vol. 48, Mar. 1997; pp. 762-767.

Corbett, et al: "Temperature Modulation (Hypothermic and Hyperthermic Conditions) and its Influence on Histological and Behavioral Outcomes Following Cerebral Ischemia"; Brain Pathology, vol. 10, 2000; pp. 145-152.

Colbourne, et al: "Delayed and Prolonged Post-Ishemic Hypothermia is Neuroprotective in the Gerbil"; Brain Research, vol. 654, May 10, 1994; pp. 265-272.

International Search Report, International Application PCT/US2005/023857; Mar. 10, 2006.

* cited by examiner

PORTABLE THERAPEUTIC COOLING SYSTEM

CROSS-REFERENCE TO RELATED APPLICATIONS

This application claims the benefit of U.S. Provisional Application No. 60/585,166 filed Jul. 2, 2004. The entire contents of the above application are herein incorporated by reference.

BACKGROUND OF THE INVENTION

1. Field of the Invention

The present invention relates generally to a cooling system and more particularly, but not by way of limitation, to a portable therapeutic cooling system utilizing gas that provides a mild hypothermic effect adapted to be used immediately or as soon as possible following a traumatic event.

2. Description of the Related Art

There are circumstances in which it may be desirable to positively cool a patient as part of clinical treatment. Benefits may arise by subjecting patients who have suffered a stroke or cardiac arrest, or other significant or life threatening health event, to mild hypothermia, e.g. a temperature in the range of 32° to 34° C. for a period of more than about 1 hour after the cardiac arrest. Because the period of time from the significant or life threatening health event to when the patient's body may be treated may be great due to extraneous circumstances, such as transportation to a hospital, it is suggested that such treatment begin as soon as possible.

Temperature is an important variable in determining the amount of neural damage resulting from an ischemic attack (Dietrich et al, 1990). Clinically, temperature is now deemed a significant, independent risk factor for stroke (Reith et al, 1996), as well as a contributing risk factor to other risk factors for stroke such as hypertension, cigarette smoking, atrial fibrillation, diabetes, and transient ischemic attacks etc. Therapeutically, the implementation of mild hypothermia (34-36° C.) to stroke and head trauma patients is advocated as beneficial based on clinical studies (Kammersgaard et al, 2000; Schwab et al, 1997) and animal experiments indicating long term neural and behavioral benefits (Corbett & Thornhill, 2000; Colbourne & Corbett, 1994).

Clinically, whole body cooling of stroke patients has been tested with forced air-cooling with the Bair Hugger® wrap and anesthetics (Kammersgaard et al, 2000) or with cooling from fans and alcohol washes (Schwab et al, 1997). Pethidine anesthetic is given to prevent shivering activation. More regionalized head cooling of head trauma and stroke patients has been attempted. Cooling helmets (previously cooled or having cooled water or air circulating through them) attempt to decrease brain temperature via conductive changes through the skull (Klatz & Goldman, 1995 in U.S. Pat. No. 5,913,885; Gunn & Gunn 1998 in PCT Patent Application WO98/56310). Cooling pillows for the head and neck region have also been devised to decrease the body temperature of the patient (Tsutomu & Koji, 1998 in Japanese Patent Publication 09-072152; Katsumitsu & Shinichi, 2000 in Japanese Patent Publication 10-250455). These devices are often bulky and require specialized knowledge of the device in order to operate the device effectively.

Review of exemplary prior devices indicates that there is a need for a device or system that cools the entire body in conjunction with a temperature monitoring system so as to regulate the cooling effect. There is a need for a device that can be quickly applied to the patient shortly after a significant or life threatening health event. Such a device is particularly necessary in a pre-hospital setting, such as during transport in an emergency vehicle.

Further, prior devices are relatively bulky and uncomfortable. In the pre-hospital setting, for example, when a subject is being transported to a hospital after injury, there is a need for a device that is comfortable and respectful of the subject's physical condition. In the case of injury to the brain induced by stroke, or in the case of cardiac arrest, a subject may be transported to a hospital over a long distance. Many such subjects are elderly and would find it uncomfortable, traumatic or even undignified to be encased in such devices as are known. Particularly, bulky helmet-like devices with circulating fluids or large cooling inserts are inappropriate for this reason. Further, the sheer size of the known devices prohibit them from becoming a standard item kept in an emergency vehicle, or in any other pre-hospital setting having a limited amount of storage space. Prior devices further rely on infusions of cold saline, which suffers from a lack of temperature control during application of the infusion.

There is a need to have a simple, body-enclosing device that may be utilized by emergency medical technicians, health-service personnel, or in the patient's immediate area (e.g. home) that can cool the body to prevent damage to critical portions of the body and minimize any after-effects of such traumatic health events prior to reaching a hospital.

BRIEF SUMMARY OF THE INVENTION

The present invention fulfills these and other needs through the development of a portable therapeutic cooling system that utilizes convective cooling and re-circulated air to efficiently, safely, and effectively cool the head and body of the patient, clothed or not, immediately after a significant or life threatening health event, such as a cardiac arrest or stroke.

BRIEF DESCRIPTION OF THE SEVERAL VIEWS OF THE DRAWING

A more complete understanding of the method and apparatus of the present invention may be obtained by reference to the following Detailed Description of the Invention, with like reference numerals denoting like elements, when taken in conjunction with the accompanying Drawings wherein.

DETAILED DESCRIPTION OF THE INVENTION

The present invention overcomes the deficiencies of the prior art through the development of a portable therapeutic cooling system adapted to be applied as soon as possible to the patient after the health event, that is adapted to be used in transitory settings, such as in an ambulance, or in a patient's immediate area, such as the patient's home, that is adapted to be operated by a bystander, paramedic, or other nearby personnel and can be used effectively on clothed patients.

Figure 1:
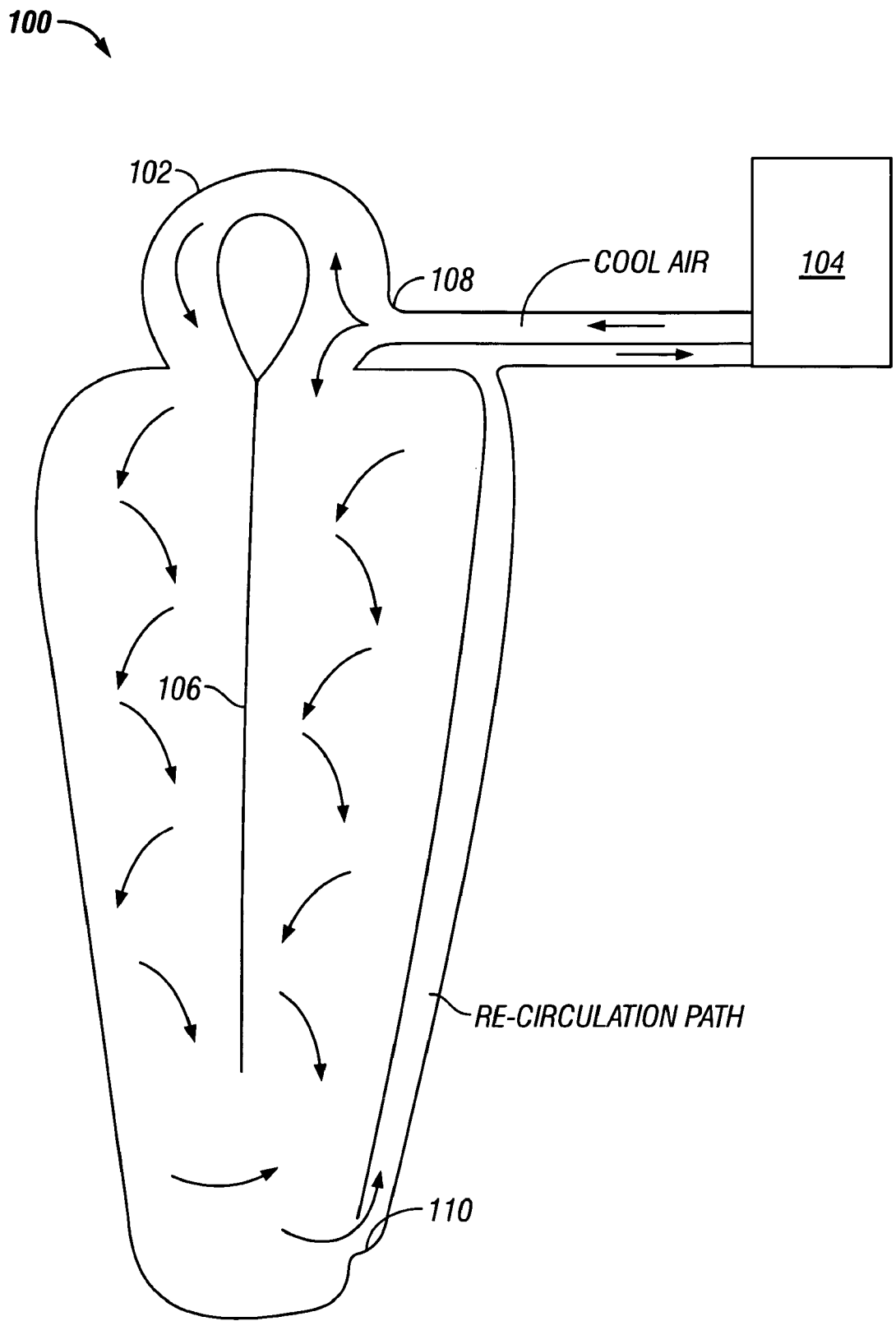
FIG. 1 is a top partial cutaway view of a portable therapeutic cooling system is shown according to one embodiment of the present invention.

Referring first to FIG. 1, a top partial cutaway view of a therapeutic cooling system is shown according to one embodiment of the present invention. The cooling system 100 includes an inflatable unitary head and body suit 102 coupled to a cooling unit 104. The inflatable suit 102 is preferably composed of disposable material capable of allowing air to circulate through the inflatable suit 102, but non-disposable embodiments are contemplated to be within the scope of this invention. The inflatable suit 102 is adapted to be sealed about the patient along a seam 106, such as by a zipper, buttons or other equivalent fastening means, although the convective nature of the heat transfer from the inflatabl e suit 102 to the patient does not require the inflatable suit 102 to be sealed about the patient in order for the patient to be cooled.

The suit 102 may be designed in small, medium, large and extra-large configurations or otherwise sized to shape pediatric patients, depending on the requirements of the user. The suit 102 is suitably adapted to circulate air throughout the suit 102 while preventing the air from escaping to the environment, and has an air inlet port 108 and an air outlet port 110. The air inlet port 108 is preferably connected to the cooling unit 104 via hoses or the like, which delivers cooled air from a source to the suit 102. The air outlet port 110 is adapted to deliver air circulated through the suit 102 to the cooling unit 104 via hoses or the like for re-circulation into the suit 102 via the air inlet port 108.

The suit 102 is adapted to deliver cooling to the patient via convective heat transfer. The suit 102 is further adapted to provide cooling to critical areas such as the neck, scalp, and groin.

When a person undergoes a traumatic health event, the bystander, paramedic or other nearby person may easily slide the clothed person into the suit 102 and close the suit 102 via the seam 106. Upon sealing, the cooling unit 104 is either activated, if already connected to the suit, or connected to the air inlet port 108 and air outlet port 110 and then activated. Cool air is then directed to flow throughout the suit and convectively cool the patient's body by encompassing a significant percentage of the patient's entire body. The re-circulation feature of the suit 102 allows the system to operate efficiently and maintain the air at a predetermined cooling temperature.

Although not specifically shown in this FIG. 1, a power source, such as a 12 V.D.C. device—such as those available in ambulances—or other power sources including A.C. current-delivering devices may be suitably used to power the cooling unit 104. Alternatively, a battery may be included in the cooling unit 104.

Figure 2:
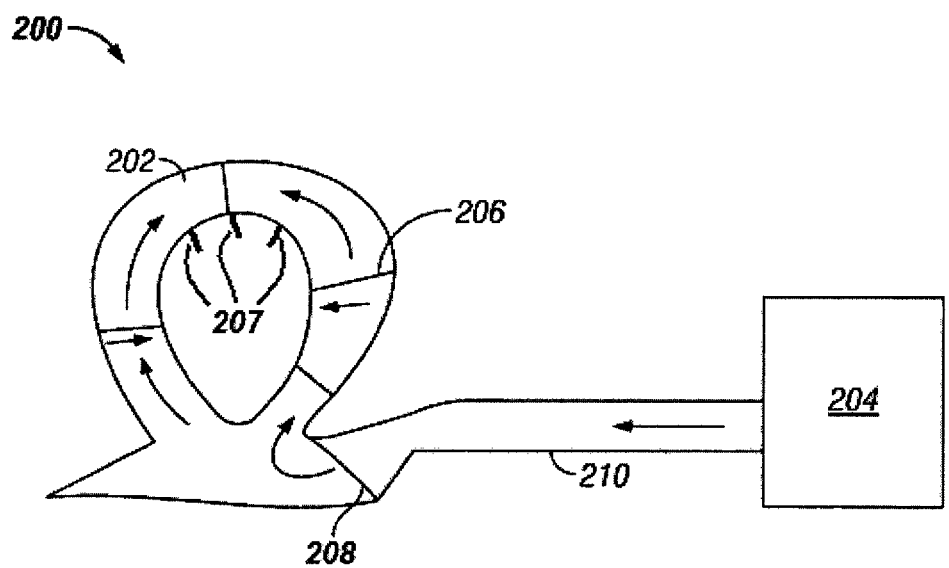
FIG. 2 is a top-plan view of a portable therapeutic cooling system in accordance with another embodiment of the present invention.

Referring now to FIG. 2, a top-plan view of a portable therapeutic cooling system 200 in accordance with another embodiment of the present invention is shown. The portable therapeutic cooling system 200 is adapted to be placed about a patient's head and neck only, and cool the head and neck, including the carotid artery. One of skill in the art will appreciate that the placement of the portable therapeutic cooling system 200 will allow other parts of the body to be cooled as well via normal blood circulation in a patient's body. As such, a hood 202 is provided connected to a cooling unit 204. The hood 202 provides convective airflow through the hood 202 around the scalp of a patient in a closed loop, and further includes means to provide a transmission path for the air in an effort to cool the patient's brain, such as emissary veins 207 in an open loop. The hood 202 further includes stretchers 206 in the fabric structure thereof to provide space for allowing circulation of air around the scalp.

An air inlet port 208 is provided on the hood 202 for connecting a delivery tube 210 to the cooling unit 204. When the cooling unit 204 is activated, cold air is delivered through the delivery tube 210 and into the hood 202, where it circulates around the head and neck area of the patient and provides convective cooling.

Figure 3:
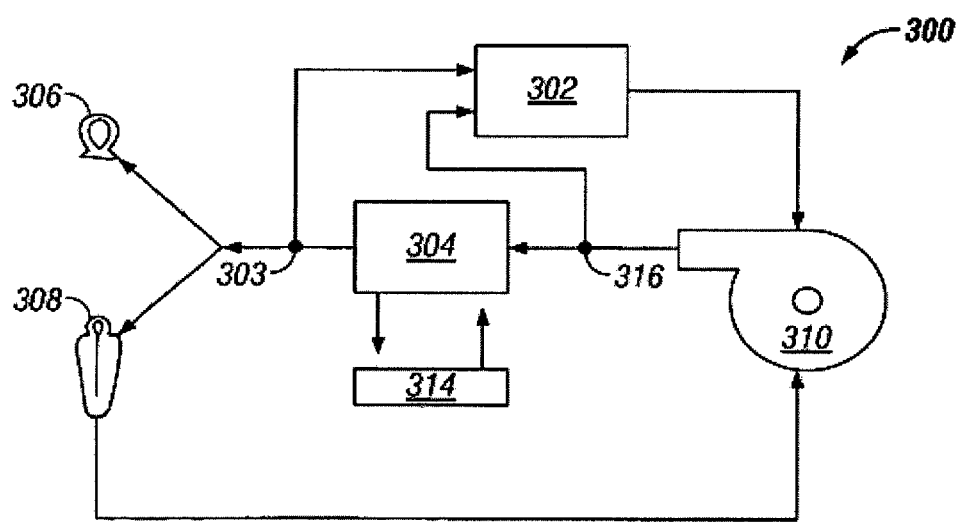
FIG. 3 is a schematic diagram of a portable therapeutic cooling system according to one embodiment of the present invention.

Referring now to FIG. 3, a schematic diagram of a portable therapeutic cooling system 300 is shown according to one embodiment of the present invention. A control unit 302 is provided, which receives temperature input from a temperature sensor 303 between a heat exchanger 304 and the output devices, such as the hood 306 and suit 308. The control unit 302 provides a speed control signal to an air blower 310, which, in turn, blows air over the heat exchanger 304 in communication with a cooling source 314. A pressure sensor 316 may be provided between the air blower 310 and heat exchanger 304 and connected to the control unit 302 to assist the control unit 302 in determining the appropriate speed of the air blower 310.

Accordingly, when the control unit 302 is activated, it first determines the temperature from the temperature sensor 303 and the pressure from the pressure sensor 316. The control unit 302 then provides a signal to the air blower 310, which activates and blows air over the heat exchanger 304. The resulting air is then transmitted to either the hood 306 or the suit 308, depending on which device is connected to the system 300.

Figure 4:
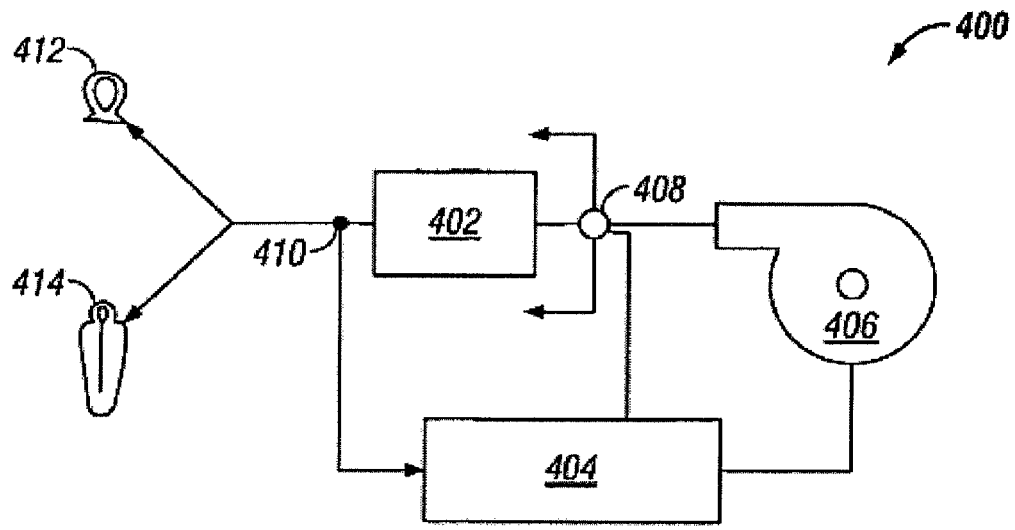
FIG. 4 is another schematic diagram of a portable therapeutic cooling system according to one embodiment of the present invention.

Referring now to FIG. 4, another schematic diagram of a portable therapeutic cooling system 400 according to one embodiment of the present invention is shown. The cooling system 400 is provided with a peltier element 402 in combination with a heat exchanger for controlling the temperature of air passing therethrough. A control unit 404 is connected to an air blower 406, a diverter valve 408 and a temperature sensor 410. The diverter valve 408 is prepositioned between the air blower 406 and the peltier element 402 and directs airflow accordingly over the hot side or cold side of the peltier element 402 based on the control unit 404 and the requirement to warm or cool. The temperature sensor 410 is placed downstream from the peltier element 402 and upstream of either the hood 412 or suit 414, depending on the configuration of the system 400. As such, the cooling system 400 provides sufficient thermal control to the patient when using the hood 412 or suit 414. It is to be appreciated that the hood 412 or suit 414 may be inflatable, and that the hood 412 or suit 414 may be unitary.

Figure 5:
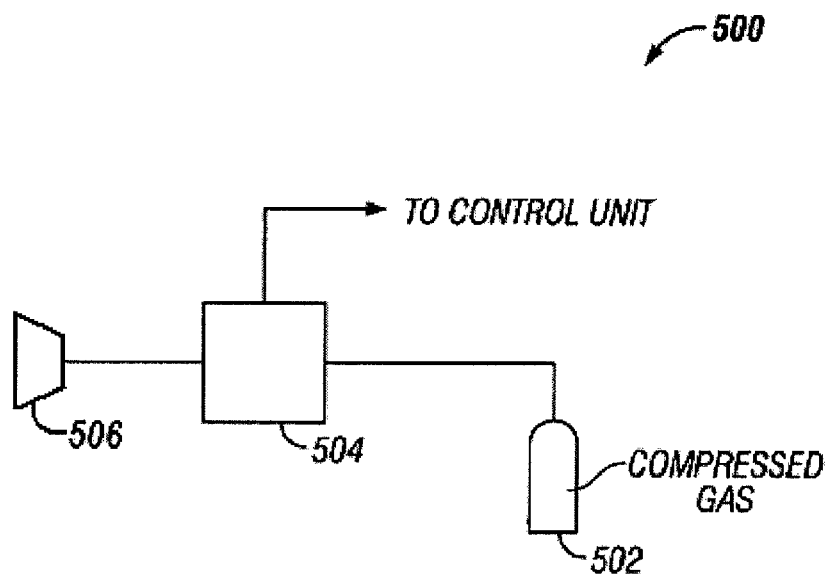
FIG. 5 is another schematic diagram of an alternate cooling system used with a portable therapeutic system according to one embodiment of the present invention.
Figure 6:
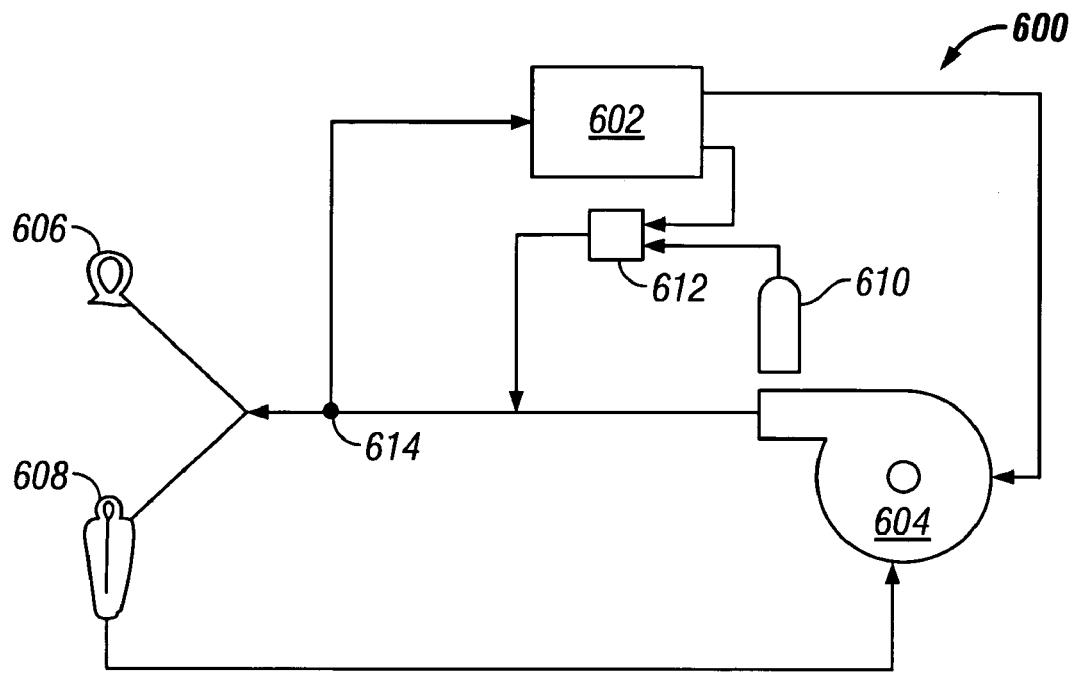
FIG. 6 is another schematic diagram of a portable therapeutic cooling system according to one embodiment of the present invention.

Referring now to FIG. 5, another schematic diagram of an alternate cooling supply 500 used with the portable therapeutic system of FIG. 6 is shown. The alternate cooling supply 500 is compressed gas, which is often stored in containers such as container 502. The container 502 is connected to a proportional valve 504, which in turn is connected to a control unit (not shown), and may be connected to a heat exchanger (not shown). Alternatively, instead of connecting to a heat exchanger, the valve 504 may be connected to a dilution device 506 to dilute the compressed gas with air. Liquid air may be used as the compressed gas.

FIG. 6 is another schematic diagram of a portable therapeutic cooling system 600 according to one embodiment of the present invention. The system 600 includes a control unit 602, an air mover 604 connected to the control unit 602 and to either a hood 606 or suit 608 as desired. A compressed gas container 610 is further provided connected to a valve 612. The valve 612 is connected to the control unit 602, and to an area upstream of the air mover 604 before the hood 606 or suit 608. A temperature sensor 614 is provided in the same area and connected to the control unit 602 for providing temperature data to the control unit 602 during operation.

When the suit 608 is used, air is re-circulated from the suit 608 to the air mover 604 to increase the efficiency of the system. The compressed gas, such as liquid air, provides a cool stream of air to the hood 606 or suit 612, and thereby eliminates the need for a heat exchanger. Flow from the container 610 is controlled by the valve 612, which in turn is directed to increase or decrease the airflow therethrough by the control unit 602. Although air is used in terminology, it is to be understood that air may comprise any gas, including fluid, capable of providing cooling to the output device. It is to be further understood that the hood 606 or suit 608 may be inflatable, and that the hood 606 or suit 612 may be unitary.

Figure 7:
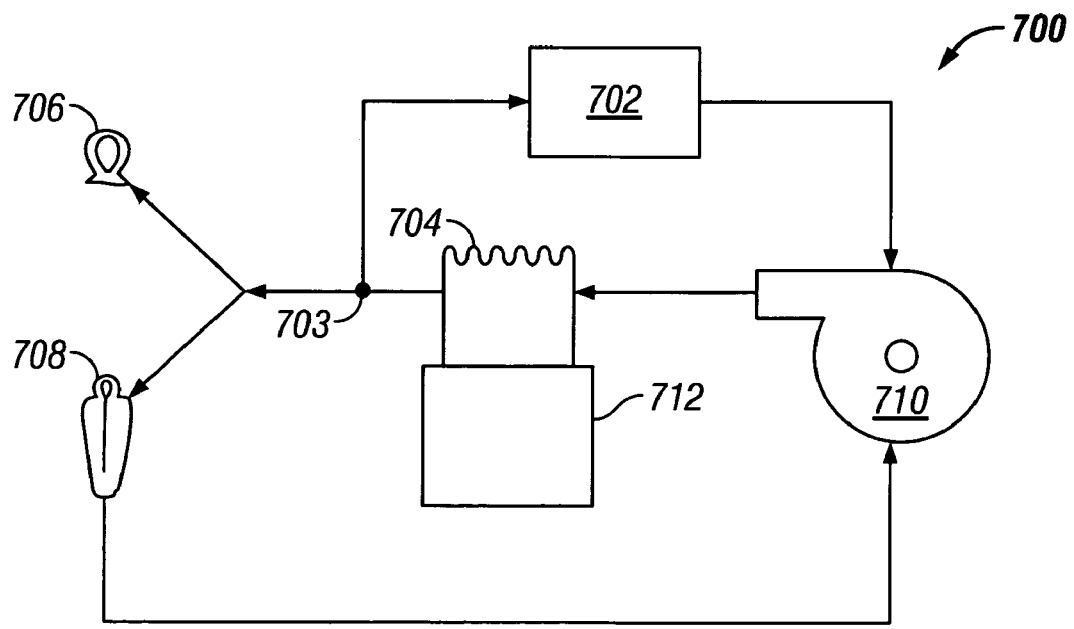
FIG. 7 is another schematic diagram of a portable therapeutic cooling system according to one embodiment of the present invention.

Referring now to FIG. 7, another schematic diagram of an alternate portable therapeutic cooling system 700 is shown. A control unit 702 is provided, which receives temperature input from a temperature sensor 703 between a heat exchanger 704 and the output devices, such as the hood 706 and suit 708. The control unit 702 provides a speed control signal to an air blower 710, which, in turn, blows air over a heat exchanger 704 in communication with ice 712. A re-circulation line may be provided between the suit 708 and the air blower 710, which may be a pump or the like, to increase the cooling efficiency of the system 700. The ice 712 provides a generally readily available cooling source for users of the system 700 in the event of emergency.

It is to be appreciated that each of the embodiments shown in the FIGURES are portable, and adapted to be disposable, though not limited to this feature. As such, the embodiments shown herein provide an efficient, portable therapeutic cooling system that may be conveniently used by bystanders, paramedics, or anyone who is available to assist after a patient undergoes a significant or life threatening health event, with little instruction required. It is further to be appreciated that the cooling disclosed herein is typical of that of a convective cooling system, though conductive, radiation or alternate heat-transfer mechanisms adapted to be portable are contemplated to be within the scope of this invention. Both the hood and suit in the embodiments shown is adapted to be disposable to avoid the necessary decontamination procedures that would normally accommodate re-use of these devices. It is to be further appreciated that when the term air is used, it encompasses any gas, including a liquid, capable of provided cooling to the respective output device (e.g. the hood, suit, and unitary head and body suit).

The previous description is of preferred embodiments for implementing the invention, and the scope of the invention should not necessarily be limited by this description. The scope of the present invention is instead defined by the following claims.

I claim:

1. A portable therapeutic cooling system, comprising:
   a thermal control unit;
   an output device coupled to the thermal control unit;
   a temperature sensor communicating with the thermal control unit and the output device;
   a cooling source connected to the thermal control unit and the output device;
   an air blower electrically connected to the thermal control and the output device; and
   a pressure sensor connected to the thermal control unit and the output device;
   wherein the thermal control unit is adapted to control the temperature in the output device;
   wherein the cooling source is compressed gas in a compressed gas container;
   wherein the compressed gas container is connected to a proportional valve; and
   wherein the proportional valve is connected to a dilution device.

2. The portable therapeutic cooling system of claim 1, further comprising a heat exchanger connected to the cooling source and thermal control unit, and to the output device.

3. The portable therapeutic cooling system of claim 2, wherein the compressed gas-container is connected to a proportional valve, which is connected to the thermal control unit and adapted to proportion the amount of compressed gas released from the compressed gas container to the output device based on input from the thermal control unit.

4. The portable therapeutic cooling system of claim 3, wherein the compressed gas is liquid.

5. The portable therapeutic cooling system of claim 1, wherein the output device is selected from the group consisting of a unitary head and body suit adapted to enclose a patient, a hood adapted to enclose a patient's head, or a body suit adapted to enclose a patient's body.

6. The portable therapeutic cooling system of claim 1, wherein the output device is disposable.

7. The portable therapeutic cooling system of claim 1, wherein the output device is inflatable.

* * * * *

UNITED STATES PATENT AND TRADEMARK OFFICE
CERTIFICATE OF CORRECTION

PATENT NO. : 7,637,931 B2 Page 1 of 1
APPLICATION NO. : 11/175084
DATED : December 29, 2009
INVENTOR(S) : Keith Patrick Heaton It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1143 days.

Signed and Sealed this

Ninth Day of November, 2010

David J. Kappos
*Director of the United States Patent and Trademark Office*